United States Patent [19]
Turecek et al.

[11] Patent Number: 5,891,843
[45] Date of Patent: Apr. 6, 1999

[54] PHARMACEUTICAL COMPOSITION FOR THE TREATMENT OF BLOOD COAGULATION DISEASES, METHODS FOR THE PRODUCTION THEREOF AND ITS USE

[75] Inventors: Peter Turecek, Klosterneuburg; Hans-Peter Schwarz, Vienna; Gerda Redl, Rutendorf, all of Austria

[73] Assignee: Immuno Aktiengesllschaft, Vienna, Austria

[21] Appl. No.: 701,755

[22] Filed: Aug. 22, 1996

[30] Foreign Application Priority Data

Aug. 28, 1995 [DE] Germany .......................... 195 31 637.1

[51] Int. Cl.⁶ .......................... A01N 37/18; A61K 38/00; A61K 35/14; C07K 1/00
[52] U.S. Cl. .............................. 514/2; 514/834; 530/381; 530/384; 424/101
[58] Field of Search .......................... 424/101; 530/384, 530/381; 514/834, 2

[56] References Cited

U.S. PATENT DOCUMENTS

| 4,287,180 | 9/1981 | Thomas | 424/101 |
|---|---|---|---|

FOREIGN PATENT DOCUMENTS

| 350 726 | 6/1979 | Austria . |
|---|---|---|
| 368 883 | 11/1982 | Austria . |
| 1547/93 | 8/1993 | Austria . |
| 0041173A1 | 12/1981 | European Pat. Off. . |
| 0 044 343 | 1/1982 | European Pat. Off. . |
| 0 082 182 | 6/1983 | European Pat. Off. . |
| 0 124 506 | 11/1984 | European Pat. Off. . |
| 0 159 311 | 10/1985 | European Pat. Off. . |
| 0159311A1 | 10/1985 | European Pat. Off. . |
| 0346241A1 | 12/1989 | European Pat. Off. . |
| 0 519 901 | 12/1992 | European Pat. Off. . |
| 0519901A2 | 12/1992 | European Pat. Off. . |
| 0 547 932 | 6/1993 | European Pat. Off. . |
| 0547932A1 | 6/1993 | European Pat. Off. . |
| 2362633 | 3/1978 | France . |
| 27 34 821 | 3/1978 | Germany . |
| 31 27 318 | 4/1982 | Germany . |
| 3740520A1 | 6/1989 | Germany . |
| 2080312 | 2/1982 | United Kingdom . |
| 82/18870 | 10/1992 | WIPO . |

OTHER PUBLICATIONS

Mariani, Russo, Mandelli, Acovated Prothrombin Complex Concentrates, Praeger, Chpt. 11 pp. 77–87, 1982.
Sander et al., Folia Haematol 117(4): 581–587 (1990), ISSN 0323–4347 Abstract only considered.
Wilms et al., Folia Haematol 117(4): 589–593 (1990), ISSN 0323–4347 Abstract only considered.
H. Vinazzer, Thrombosis Research 26:21–29 (1982).
Meili et al., Schweiz Med Wochenschr 125: 405–411 (1995) Abstract only considered.
Research Disclosure 269: 94–95 (Sep. 1986), Great Britian.
Rote Liste 1993.
Mariani et al., "Contact Activation and Factor VII After the Use of an Activated Prothrombin Complex Concentrate (FEIBA) in Hemophiliacs w/Inhibitors", Thromb. Res. vol. 31, (1983), pp. 475–488.
Teitel, "The Factor VIII Bypassing Activity of Prothrombin Complex Concentrates: the Roles of Factor of VIIa and of Endothelial Cell Tissue Factor", Throm. & Hemo., vol. 66, No. 5, (1991), pp. 559–564.
Headner et al., "Clinical Experience with Human Plasma–Derived Factor VIIa in Patients with Hemophilia A and High Titer Inhibitors", Hemostasis, vol. 19, (1989), pp. 335–343.
Vinazzer, "Comparison Between Two Concentrates with Factor VIII Inhibitor Bypassing Activity", Thrombosis Research, vol. 26, (1982), pp. 21–29.
Deijk, "Evaluation of a Coagulation Assay Determing the Activity State of Factor VII in Plasma", Hemostasis, vol. 13, (1983), pp. 192–197.
Morrissey et al., "Quantitation of Activated Factor VII Levels in Plasma Using a Tissue Factor Mutant Selec. Deficient in Promoting Factor VII Activation", Amer. Soc. Hemato., vol. 81, No. 3, (1993) pp. 734–744.
Bradford, "A Rapid and Sensitive Method for the Quantitation of Microgram Quantites of Protein Utilizing the Principle of Protein–Dye Binding", Anal Biochem., vol. 72, (1976), pp. 248–254.
Giles et al., "A Canine Model of Hemophilic (Factor VIII:C Deficiency) Bleeding", Blood, vol. 60, No. 3, (1982), pp. 727–730.
Curling, "Albumin Purification by Ion Exchange Chromatography", Methods of Plasma Protein Fractionation, Academic Press, (1980), pp. 77–97.

*Primary Examiner*—Cecilia J. Tsang
*Assistant Examiner*—Jennifer Haru
*Attorney, Agent, or Firm*—Foley & Lardner

[57] ABSTRACT

The invention relates to a pharmaceutical composition for the treatment of patients with blood coagulation diseases which are caused by coagulation factor deficiency and/or inhibitors of coagulation factors, whereby the composition has a FEIB-activity and is characterized in that it has Factor VII*a* and at least one further active ingredient and the activity of at least 10 Factor VII*a* units per unit FEIBA. Additionally, the invention comprises a method for the production of the pharmaceutical preparation and its use.

13 Claims, 1 Drawing Sheet

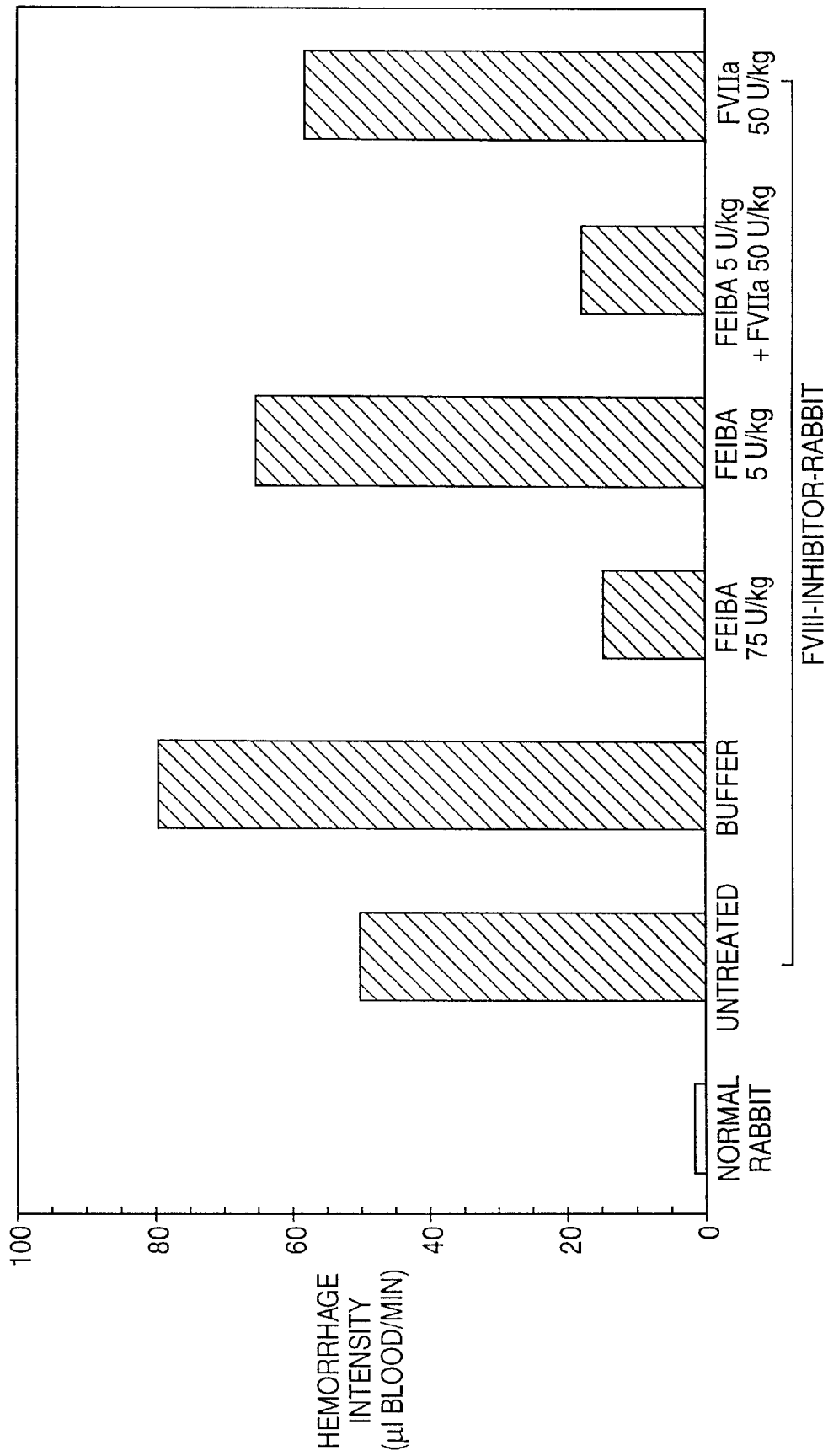

PHARMACEUTICAL COMPOSITION FOR THE TREATMENT OF BLOOD COAGULATION DISEASES, METHODS FOR THE PRODUCTION THEREOF AND ITS USE

The invention relates to a pharmaceutical composition for the treatment of blood coagulation disorders, especially of Factor VIII inhibitor patients. The invention further relates to a method for production of a composition of this type as well as its use.

Blood coagulation is triggered by a series of successive reactions of various proteins and/or enzymes. The formation of fibrin from fibrinogen and, therewith, the closure of wounds is prevented by a lack of blood coagulation factors; the consequence is hemorrhage. Such a case exists with hemophilia A. This is the most widespread bleeding disorder and is caused by a deficiency in Factor VIII. Factor VIII containing preparations are used for replacement therapy in hemophilia A. Treatment with these preparations leads to a rapid cessation of bleeding in most cases.

However, there are also patients among which not only a deficiency in Factor VIII occurs, but also who have developed an inhibitor directed against Factor VIII. A further collection of patients posses Factor VIII inhibitors without suffering from hemophilia A. Depending on the amount of factor A inhibitors present, the effect of administered Factor VIII is inhibited by its neutralization.

Presently, preparations based on a plasma fraction which contains a mixture of coagulation factors are offered for treatment of Factor VIII inhibitor patients. This plasma fraction can contain, for example, factors of the prothrombin complex (Factor II, VII, IX, X). A blood coagulation promoting preparation with Factor VIII inhibitor bypass activity (FEIBA® TIM 4, Immuno AG) is obtained, according to AT-0 368 883 for example, by treatment of cryosupernatant. This preparation also contains coagulation Factors II, VII, IX, X.

The action of a FEIBA preparation is complex due to its complex composition. Mariani et al (Thromobosis Res. 31, 475–488, (1983)) mentions Factor VII in its activated form as a principle of action. It was established that a higher content of Factor VIIa in plasma occurs in hemophiliacs after infusion of a FEIBA preparation.

Equally, the role of Factor VIIa in prothrombin complex concentrates with a "Factor VIII-bypassing-activity" is discussed by Teitel (Thrombosis and Haemostasis 66 (5) 559–564, (1991)). Simultaneously, the principle of action of Factor Xa in preparations of this type is also dealt with. The examined prothrombin complex concentrates contained Factor VIIa, expressed by the ratio of Factor VII activity to Factor VII antigen of 2.1 and 2.5.

The therapeutic composition containing prothrombin produced according to EP-0 044 343-B1 is suitable for treatment of coagulation factor inhibitors and contains an activated prothrombin complex in which the factors are partially activated. The amount of Factor VIIa is between 8–80 units per ml. Factor IX concentration is in the range of 15 to 112 units per ml. Correspondingly, the content of Factor VIIa, with respect to Factor IX, is 0.07–5.3 U Factor VIIa/U Factor IX. Vinazzer (Thromobosis Res. 26:21–29 (1982)) demonstrates the difference of the preparations AUTOPLEX, which is produced according to EP-44 343 and FEIBA. As shown there, AUTOPLEX is distinguished by the higher content of thrombin (Factor IIa) measured in NIH units in comparison to FEIBA (see table 1, page 24).

However, highly purified Factor VIIa preparations are also proposed for therapy of coagulation factor inhibitor conditions (for example, EP 0 082 182-B1) and Hedner et al. (Haemostasis 19, 335–343 (1989)).

A method for the production of a concentrate which contains highly purified Factor VIIa is also described in EP 0 547 932-A1. Factor VII is separated from coagulation Factors II, IX and X by anion exchange chromatography of a cryoprecipitate. Factor VII is then subjected to a further purification and activation, whereby the addition of exogenous proteins is avoided. Subsequently, Factor VIIa is treated for inactivation of viruses by a treatment with an organic solvent/detergent (TnBP/Tween).

The risk of transmitting infectious agents exists by the use of plasma or a plasma fraction as the starting material for the production of pharmaceutical preparations. Despite selection of donors and tests of the individual plasma donations for possibly present viruses, such as HIV, hepatitis B or hepatitis C virus, the possibility exists that a plasma pool is infectious. This residual infectivity is not to be ruled out because of limited sensitivity of the test systems, but also because of the incubation time until the appearance of measurable infection markers (diagnostic window).

Pharmaceutical preparations which are prepared from plasma or a plasma fraction are therefore subjected to diverse treatments for inactivation of viruses potentially present. A proven method for the inactivation of membrane enveloped as well as non-membrane enveloped viruses is described in EP 0 159 311-B1. Thereby, a pharmaceutical preparation is heated in a solid state after adjustment of a water content to a value of 5–70%. This treatment is also described as a steam (vapor) treatment. Instead of water, methanol or ethanol can also be used.

However, combinations of virus inactivation methods are equally possible. According to EP 0 519 901, a treatment with highly concentrated tensides is combined with a heat treatment.

An object of the invention is to provide an improved pharmaceutical composition for treatment of blood coagulation disorders, especially of Factor VIII inhibitor patients as well as a simple method for its production.

The object is achieved according to the invention by a pharmaceutical composition with FEIB-activity which contains Factor VIIa and at least one further active ingredient and has the activity of 10 Factor VIIa units per unit FEIBA.

The content of Factor VIIa in the composition according to the invention is at least 10, preferably 10 to 100, most preferably 10 to 20, especially 10 to 15, units per unit FEIB-activity. The FEIB-activity is determined by means of a method according to AT-350 726.

It has turned out that a preparation which contains highly purified Factor VIIa as the sole effective substance does not possess any FEIB-activity. Therefore, it was surprising that addition of Factor VIIa to a preparation with FEIB-activity, such as one of the activated prothrombin complex containing fractions, contributes to a substantial improvement of the effectiveness of a pharmaceutical preparation for the treatment of blood coagulation diseases, especially of Factor VIII inhibitor patients.

The content of Factor VIIa was determined in the following examples with the methods described by van Deijk (Haemostasis 13: 192–197, 1983) and EP 0 547 932 with bovine thromboplastin. Additionally, Factor VIIa can also be determined by using recombinant, soluble tissue factor according to the methods of Morrissey et al. (Blood 81: 734–744, (1983)) and WO 92/18870.

Coagulation Factors II, IX and X and, additionally for example, tissue factor or Xa and phospholipids are to be named as active ingredients in a preparation of FEIB-activity. The above listing of substances in a preparation with FEIB-activity is not complete and, therefore, should not be considered as limiting.

The preparation according to the invention preferably contains coagulation Factors II, IX and X, preferably in a concentration which corresponds to a ratio of 0.5–2, particularly preferred 0.5–1.5 U/U FEIBA for each factor. The measurement is carried out according to the test description in AT-350 726.

Therewith, the composition according to the invention differs from known preparations not only in its extraordinary high ratio of Factor VIIa to FEIBA, but also in its ratio of Factor VIIa to Factor IX. For example, the latter is distinctly higher than in EP-0 044 343.

It is of further advantage when the preparation according to the invention additionally contains protein C and/or protein S.

It was surprising that the preparation according to the invention can be produced in a simple and economic manner. Therefore, the invention also comprises a production method which is characterized by contacting a fraction as illustrated above with an anion exchanger, whereby coagulation Factor VII is at least partially activated. Conditions are selected thereby which allow for the simultaneous adsorption of Factor VII and/or Factor VIIa with coagulation Factors II, IX and X, for example, by using buffers of low ionic strength. Subsequently, the anion exchanger is separated, for example by sedimentation, and the fraction which contains coagulation Factors II, VIIa, IX and X is isolated. In this connection, the fraction already possesses FEIBA before contact and/or a FEIBA is generated in the fraction during this.

Preferably, a strong anion exchanger, for example a matrix with quaternary ammonium groups such as QAE, TMAE and Q groups, is used as an anion exchange material. As a support for the anion exchange groups, cross-linked Dextran, such as Sephadex® or Sepharose® or synthetic material such as Fraktogel® is used.

This method of production is distinguished, among others, by its economic procedure. The method has the advantage that coagulation Factor VII must not be separated at first in order to then be added to the preparation again. Additionally, the coagulation factor-containing fraction is not only purified, but coagulation Factor VII is also activated in one step. Partial activation of Factor IX and Factor X, but not of Factor II, also occurs at the same time.

The composition according to the invention is also obtainable by combining a fraction containing a purified prothrombin complex and a fraction containing purified Factor VIIa, and by a treatment for the inactivation of viruses. However, the pharmaceutical composition according to the invention can also be composed of a fraction containing a purified partial prothrombin complex (Factors II, IX and X) and a fraction containing purified Factor VIIa, whereby it is treated for the inactivation of viruses. The prothrombin complex used for the production of the composition according to the invention is preferably present as activated prothrombin complex or as a FEIBA preparation. In an activated prothrombin complex, coagulation Factors II, IX and X are partially activated. However, the activation of Factor II is to be avoided in such a preparation in order to directly exclude prothrombogenic activity.

By using certain conditions such as high ionic strength in the starting solution and/or in the washing buffer and strong anion exchange gels, for example Q-Sepharose® Fast Flow (Pharmacia), activated prothrombin complex can be isolated as a FEIBA preparation with higher yields from plasma or plasma supernatant after separation of the cryoprecipitate. Gels of this type then bind Factor VII or Factor VIIa relatively poorly. Therefore, Factor VIIa can be isolated from the same starting material in a further process with higher yields.

The fractions obtained are processed to pharmaceutical preparations in the customary manner, for example, by addition of pharmaceutically acceptable carriers and/or adjuvants, sterile filtered and lyophilized to storable pharmaceutical preparations.

The composition according to the invention can be produced by a further method with the following steps:

a) isolating coagulation Factors II, IX and X as individual components or as a mixture from one or more starting materials containing one or more of coagulation Factors II, IX and/or X, b) isolating coagulation Factors VII/VIIa from a starting material containing coagulation Factor VIIa and/or coagulation Factor VII, whereby coagulation Factor VII is at least partially activated, c) pretreating or treating the starting materials or the isolated coagulation factors for inactivation of infectious agents, and d) mixing the isolated coagulation factors together with a pharmaceutically acceptable carrier.

In a preferred embodiment, Factor VIIa is added to prothrombin complex, which can also be present as partial prothrombin complex, after purification of the components and mixed with a pharmaceutically acceptable carrier, and subsequently subjected to a treatment for virus inactivation, for example a heat treatment.

The addition and/or content of highly pure Factor VIIa is especially advantageous because less contaminating proteins are introduced into the preparation as impurities therewith. The specific activity of Factor VIIa in the preparation is preferably more than 10 U/mg to 1,000 U/mg protein.

The prothrombin complex is preferably present as an activated prothrombin complex or FEIBA preparation.

Preferably, a heat treatment, for example a steam treatment, is carried out for inactivation of infectious agents (viruses). Thereby, it has turned out that a heat treatment of the coagulation factors in a solid state can be conducted without addition of stabilizing proteins, such as albumin. Factor VIIa is surprisingly stable enough that it can also be treated in a purified state for inactivation of infectious agents.

The heat treatment for inactivation of viruses has the advantage that not only lipid coated viruses are inactivated, but also viruses which are not surrounded with a lipid envelope.

The method according to the invention is characterized in that Factor VIIa can be isolated from a fraction which accumulates as a by-product in the production of a fraction containing (partial) prothrombin complex. Therefore, this method is also particularly distinguished by its economic efficiency.

With the method according to the invention, it is possible to obtain all components of the composition according to the invention from a single starting material, preferably a plasma pool or a plasma fraction. Therewith, the safety of the pharmaceutical compositions obtained according to the invention is increased.

In a preferred embodiment, the method according to the invention intends isolation of coagulation Factor VII through chromatographic methods, preferably by means of anion exchangers, such as DEAE-Sephacel®, DEAE-Sephadex®, DEAE-Sepharose® CL6B, DEAE-Sepharose®

Fast Flow, QAE-Sephadex®, QAE-Sepharose® Fast Flow, Q-Sepharose® High Performance, Q-Sepharose® Big Beads (obtainable from Pharmacia); DEAE-Tris Acryl, DEAE-Spherodex®, Q-Hyper-D (obtainable from Sepracor); Macroprep® DEAE, MacroprepQ® (BioRad); DEAE-Toyopearl®, QAE-Toyopearl®, Poyopearl® Super-Q (Tosohaas), Protein PAK DEAE (Waters), Fractogel® EMD-TMAE, Fractogel® EMD-DEAE, Fractogel® EMD-DMAE, Licrospher® 1000 TMAE, Licrospher® 1000 DEAE and Licrospher® 4000 DMAE (Merck). A particularly preferred embodiment relates to the isolation of Factor VIIa by hydrophobic chromatography, for example by using the following materials: Butyl-Sepharose®, Octyl-Sepharose®, Phenyl-Sepharose®, Phenyl-Sepharose® Fast Flow High Sub, Phenyl-Sepharose® Fast Flow Low Sub, Phenyl-Sepharose® High Performance (all obtainable from Pharmacia); Fractogel® TSK-Butyl (Merck); Macroprep®-Methyl-HIC-Support, Macroprep®-t-Butyl-HIC-Support (BioRad), TSK-Gel Butyl Toyopearl®, TSK-Gel Phenyl Toyopearl®, TSK-Gel Ether Toyopearl® (Tosohaas). A simultaneous activation—at least partially—during the isolation is advantageous in the purification of coagulation Factors IX and X exactly as with coagulation Factor VII. However, attention is to be paid that the preparation has no thrombogenic activity; hence, a content of activated Factor II is to be avoided.

The composition according to the invention advantageously has a FEIB-activity in the range of 1–1000 units FEIBA/ml of ready-to-use solution. Preferably, the FEIB-activity is more than 5 U/ml, most preferably a FEIBA is in the range of 10 to 100 U/ml.

The invention also comprises the use of a combination of Factor VIIa and at least one active ingredient for the production of a pharmaceutical composition with FEIB-activity for rapid cessation of hemorrhages in patients with a coagulation factor deficiency. A rapid termination of bleeding which is dependent on inhibitors of coagulation factors is especially effected by this use.

The in vivo effect of the pharmaceutical preparation according to the invention can be demonstrated in an animal model in which rabbits are temporarily placed in a hemophilia A state after treatment with a Factor VIII inhibitor plasma. In pre-treated animals of this type which have hemorrhagic diathesis corresponding to one of the inhibitor hemophilias, the abnormal hemorrhage behavior can be corrected to that of an untreated rabbit by administering 75 to 100 units FEIBA/kg. In order to demonstrate the improved effectiveness of a FEIBA preparation with a defined higher Factor VIIa content, the pharmaceutical preparation according to the invention containing FEIBA and Factor VIIa in a ratio of 10 units Factor VIIa per unit FEIBA was administered to hemorrhaging rabbits at a dose of 5 U FEIBA/kg (corresponding to 50 U Factor VIIa/kg). The hemorrhage intensity is reduced to the same extent as by the administration of 75 U FEIBA/kg.

As controls, conventional FEIBA in a dose of 5 U/kg or Factor VIIa in a dose of 50 U/kg is administered which does not lead to any noticeable reduction of hemorrhage intensity in relation to the untreated hemophilia A inhibitor animal in each case. Therewith, an unexpectedly high effectiveness of the pharmaceutical composition according to the invention is documented. An essential advantage thereby is that the thrombogenic potential of the pharmaceutical composition according to the invention is clearly reduced in comparison to conventional FEIBA.

BRIEF DESCRIPTION OF DRAWING

FIG. 1 depicts the effect of various compositions on hemorrhage intensity in a Factor VIII inhibitor rabbit.

The invention is more closely described by the following examples.

EXAMPLES 1 to 8

Method for the production of a Factor VIIa preparation

Example 1

Separation of cryoprecipitate and FEIBA from Plasma Production occurs based on AT-350 726 and AT-368 883.

Fresh, frozen, human citrated plasma was thawed at 0°–+4° C. and the cryoprecipitate resulting therefrom was separated by centrifugation at +2° C. At native pH-value, 0.5 g of DEAE-Sephadex® A-50 were added to the cryosupernatant resulting therefrom at +4° C. under continuous stirring. The suspension was stirred for a further hour and subsequently allowed to stand such that the protein-DEAE-Sephadex® complex sedimented. Thereby, FEIBA was generated and absorbed onto DEAE-Sephadex® together with the factors of prothrombin complex (II, VII, IX and X) and inert protein. The DEAE-Sephadex®-protein complex was separated from the supernatant after the completed adsorption process by centrifugation or filtration. As described in AT368883, FEIBA was isolated by washing and elution of the DEAE-Sephadex®-protein complex. The supernatant was processed further to Factor VIIa preparation.

Example 2

Separation of Factor VII/VIIa from FEIBA supernatant

After FEIBA separation from example 1, prothrombin complex factors, especially Factors VII and VIIa were then isolated from the supernatant by adsorption to aluminum hydroxide. Per 1 liter FEIBA supernatant, 10 ml of 2% aluminum hydrogel suspension were centrifuged (SORVALL RC3B, Rotor H6000A, 5000 rpm, 10 minutes, about 4° C.). The precipitate resulting therefrom was homogeneously mixed with the amount of FEIBA supernatant to be treated (Ultra Turrax). Subsequently, this was stirred for 30 minutes at 20°–22° C. and centrifuged thereafter (SORVALL RC3B, Rotor H6000A, 5000 rpm, 10 minutes, about 4° C.).

The centrifuged precipitate was suspended with 3,5% of the volume of FEIBA supernatant used for the absorption in a solution of 4 g Na$_3$Citrate.2H$_2$O/l and 7 g NaCl/l, pH 7.5, and stirred for 30 minutes for the removal of protein. Thereafter, the precipitate was separated by centrifugation (RC3B, Rotor H6000A, 5000 rpm, 10 minutes, about 4° C.). The supernatant was discarded and the precipitate was used for further processing. Subsequently, a step for the inactivation of possibly present pathogenic substances was conducted according to AT-A1547/93. Tween® 80 was presented in an amount of 1.5 volume % of the FEIBA supernatant used for the absorption and heated to 55° C. The supernatant after the first washing was suspended in the Tween® 80 solution by means of an Ultra Turrax mixer during 1–2 minutes and stirred for 10 minutes at 55° C. Thereafter, this was immediately diluted with 9-fold volumes of water (+4° C.).

The treated Al(OH)$_3$-protein complex was separated by centrifugation, the supernatant was discarded, and the precipitate was further processed. Subsequently, two washings each with 3.5 volume % of the employed FEIBA supernatant were conducted by resuspension and renewed centrifugation with citrate buffer (4 g Na$_3$Citrate.2H$_2$O/l and 7g NaCl/l, pH 7.5).

The fraction containing Factor VII/VIIa was separated from the aluminum hydroxide gel by elution with phosphate buffer. The protein-aluminum hydroxide complex was stirred for 30 minutes with 1 volume % of the FEIBA supernatant used for the absorption of 0.3M phosphate buffer, pH 8.6 (53.4 g Na$_2$HPO$_4$.2H$_2$O/l was adjusted to pH 8.6 with a solution of 41.4 g NaH$_2$PO$_4$.H$_2$O/l). Subsequently, the solid phase was separated by centrifugation at 5000 rpm for 10 minutes at 20°–22° C. The supernatant contained Factor VII/VIIa and was further processed for subsequent purification.

Example 3

Activation of Factor VII and ion exchange purification of Factor VIIa

The eluate isolated in example 2 was diluted with distilled water in a ratio of 1:1, mixed with 0.25 mM CaCl$_2$ and the pH value was adjusted to 8.6. The solution was subsequently mixed with 65 ml/l of Q-Sepharose® FF, prewashed with buffer, and stirred for 2 hours at 4° C. Subsequently, the gel to which Factor VIIa was now bound was separated by filtration or centrifugation. The loaded gel was freed from inert protein by resuspension for 15 minutes and subsequently separation from a wash buffer (96.7 g Na$_2$HPO$_4$.2H$_2$O/l and 0.0368 g CaCl$_2$.2H$_2$O/l were adjusted to pH 8.6 with a solution of 20.7 NaH$_2$PO$_4$.H$_2$O/l). Subsequently, Factor VIIa was eluded by elution with a solution of 105.7 g (NH$_4$)$_2$SO$_4$/l, 58.5 g NaCl/l and 2.42 g TrisHCl/l, pH 7.4, by suspension for 30 minutes. The gel supernatant containing Factor VIIa was separated by filtration or centrifugation.

Example 4

Purification of Factor VIIa by hydrophobic chromatography

The solution containing Factor VIIa from example 3 was chromatographically purified over Phenylsepharose® LS. A column with 50 mm ID and 24 mm bed height was filled with Phenylsepharose® LS and equilibrated in a buffer containing 2.42 g TrisHCl/l and 105.7 g (NH$_4$)$_2$SO$_4$/l , pH 7.4). 100 ml of the eluate containing Factor VIIa from example 3 was pumped over the gel with a flow rate of 23 ml/min. Thereby, Factor VIIa was bound to the gel; inert protein was found in the through-flow. The gel was washed with the buffer used for equilibration. Subsequently, Factor VIIa was eluded with a solution of 2.42 g TrisHCl/l, pH 7.4. Thereby, fractions were collected. The fractions containing Factor VIIa activity were combined and buffer exchange was carried out by chromatography over Sephadex® G-25 against a buffer containing 2.42 g TrisHCl/l, pH 7.4.

Example 5

Purification of Factor VIIa by chromatography on Q-Sepharose®

Q-Sepharose® FF, packed in a column with 25 mm ID and 55 mm bed height, was equilibrated with 20 mm TrisHCl/l, pH 7.4. Subsequently, 43 ml of the solution containing Factor VIIa from example 4 were pumped over the column with a flow rate of 5.3 ml/min. Thereby, Factor VIIa was bound to the gel, whereas inert proteins remained in the through-flow. Subsequently, this was washed with a buffer containing 25 mM Na$_3$Citrate.2H$_2$O and 80 mM NaCl, pH 6.0. Further inert protein was separated thereby. The elution of Factor VIIa was conducted by washing the column with 25 mM Na$_3$Citrate.2H$_2$O and 160 mM NaCl, pH 6.0. The protein and the fractions containing Factor VIIa activity of this elution step were pooled. Subsequently, the column was regenerated with a buffer (25 mM Na$_3$Citrate.2H$_2$0 and 1M NaCl, pH 6.0) and used further.

Example 6

Ultraconcentration of Factor VIIa preparation

The pool containing Factor VIIa from example 5 was adjusted to pH 7.0 and mixed with 0.1% human albumin. Subsequently, this was concentrated to 1/10 of the starting volume over ultra filtration membranes (Amicon YM 10, cut-off 10,000 D) under a pressure of 3.0 bar in an AMICON 80/50 stirring cell. The concentrated solution containing Factor VIIa was subsequently lyophilized.

Example 7

Heat treatment of lyophilized Factor VIIa

For the inactivation of possibly included pathogen, the lyophilized Factor VIIa preparation from example 6 was heated according to the method in patent EP 159 311 under elevation of the partial water pressure, and/or following the treatment at 60° C., also treated for a further hour at 80° C. The yield of Factor VIIa was more than 90% in each case.

Example 8

Characterization of the Factor VIIa preparation

Measurement of the degree of activation of Factor VII was carried out according to the method described by van Deijk, Haemostasis 13:192–197 (1983). The coagulation test is based on the use of bovine thromboplastin on one hand and human thromboplastin on the other hand in connection with a Factor VII depleted plasma. As a standard, measurement was done with normal human plasma. The specific activity of Factor VIIa for the individual steps of production and purification as well as the activation grade, Factor VII measured with bovine thromboplastin against Factor VII measured with human thromboplastin, are given in Table 1. The protein measurements were conducted according to the method of Bradford, Anal. Biochem. 72:248–254 (1976).

Example 9

Combination of FEIBA and Factor VIIa

Fresh, frozen, human citrate plasma was thawed at 0°–40° C. and the resulting cryoprecipitate was separated by centrifugation at +2° C. At native pH-value, 0.5 g of DEAE-Sephadex A-50 at +4° C. was added to the supernatant resulting therefrom under constant stirring. The suspension was stirred for a further hour and subsequently allowed to stand such that the protein-DEAE-Sephadex complex sedimented. Thereby, FEIBA was generated and absorbed to DEAE-Sephadex® together with the factors of prothrombin complex and inert protein. The DEAE-Sephadex®-protein complex was separated from the supernatant by filtration after the completed absorption process. As described in AT 368 883, FEIBA was desorbed from DEAE-Sephadex® by washing with buffer and subsequent elution with sodium chloride solution. The solution containing FEIBA was concentrated to 1/5 of the starting volume by ultrafiltration and subsequently incubated for auto activation of the prothrombin complex factors for 20 hours at room temperature. Subsequently, the solution containing activated prothrombin complex was lyophilized. Then, the powder was dissolved to a concentration of 30 mg protein/ml in a buffer of 2 g Na$_3$Citrate.2H$_2$O and 4 g NaCl, pH 7.2. This solution was filtered through a filter with a pore size of 1 μm and re-lyophilized. The powder isolated in this manner was dissolved in a solution containing factor VIIa which was produced as described in example 4. The solution was adjusted such that 10 U FVIIa were contained per 1 U FEIBA, tested according to AT 350 726. This mixture was re-lyophilized according to the method of EP 159 311, and treated for 10 hours at 60° C. and 1 hour at 80° C. FEIB-activity and the FVIIa activity of the powder were measured before and after the heat treatment. After the heat treatment step, the activity of FVIIa in the preparation was 96% of the starting material and had decreased by 4% therewith; the FEIB-activity was 90%, corresponding to a loss of 10%. As a comparison for this, the FVIIa preparation from example 4 was lyophilized and also heat treated. The activity decreased by 48% thereby.

Example 10
Combination of prothrombin complex and Factor VIIa

A preparation containing prothrombin complex was prepared according to the method of H. G. J. Brummelhus, Methods of Plasma Protein Fractionation, J. M. Curling (Hrsg.), page 117–128, Academic Press 1980. The preparation contained Factor II, IX and X in a similar relationship. Subsequently, the preparation was mixed with Factor VIIa which was produced as described in example 4. The mixture was adjusted in such a manner that 10 U FVIIa were contained per 1 U FX. A freeze-dried powder of this mixture was treated according to the method of Epn 159 311 for 10 hours at 60° C. and 1 hour at 80° C. The activity of coagulation Factors II, IX and X and Factor VIIa were measured respectively before and after the heat treatment. The losses of activity were 7% for Factor II, 12% for Factor IX, 3% for Factor X and 1% for Factor VIIa.

As a comparison for this, Factor VIIa preparation from example 4 was lyophilized and also heat treated. The activity decreased by 48% thereby.

Example 11
Isolation of a Factor VIIa/FEIBA preparation

A preparation containing Factor VIIa and FEIB-activity was isolated as follows. Fresh, frozen, human citrate plasma was thawed at 0°–+4° C. and the resulting cryoprecipitate was separated by centrifugation at +2° C. At native pH, the cryosupernatant resulting therefrom was mixed with 0.5 g of QAE-Sephadex® A50 (Pharmacia) and stirred at +4° C. for 15 hours. Subsequently, the gel-protein complex was separated from the supernatant by sedimentation and filtration and the fraction containing Factor VIIa and FEIBA was isolated by elution with 3% NaCl solution. Factor VIIa and FEIBA were quantitatively measured. The preparation contained 12.7 U FVIIa per unit FEIBA.

Example 12
Isolation of a Factor VIIa/FEIBA preparation

FEIBA was isolated as described in example 11. However, Fractogel® EMD TMAE (Merck) was used as an ion exchanger for the absorption in a concentration of 5 ml moist gel per liter cryosupernatant. After elution of the activated prothrombin complex factors with 3% NaCl solution, this contained 54 U FEIBA/ml as well as 0.6 U Factor VIIa/U FEIBA. In order to produce the preparation according to the invention, Factor VIIa according to examples 2–4 was isolated from the cryosupernatant and the solution containing FEIBA was added such that at least 10 U Factor VIIa/U FEIBA were finally contained.

Example 13
Isolation of a Factor VIIa/FEIBA preparation

Analogous to example 12, FEIBA was produced again. As an ion exchanger, Q-Sepharose® Fast Flow (Pharmacia) was used in a concentration of 5 ml per liter cryosupernatant. The FEIB-activity in the obtained eluate was 1.280 U/ml and 0.3 U Factor VIIa/U FEIBA. In order to produce a preparation with 20 U Factor VIIa/U FEIBA, Factor VIIa was produced, as in example 11, from the same cryosupernatant from which the FEIBA preparation was isolated and mixed with the solution containing FEIBA.

Example 14
In vivo effectiveness of a Factor VIIa/FEIBA preparation

A combination of FEIBA and Factor VIIa produced according to example 9 was tested in rabbits with Factor VIII inhibitor hemophilia as follows. Approximately 2 kg, white, New Zealand rabbits were anesthetized. After onset of the anesthesia, the right femoral vein of each rabbit was prepared and a permanent venous access was created. Through this, 0.5 ml/kg body weight of a human Factor VIII inhibitor plasma (1500 Bethesda units/ml) was infused over 10 minutes. 30 minutes after completion of the infusion, the hemorrhage characteristics were measured with a modified method according to Giles et al, Blood 60:727–730 (1982). For this, the fur around a claw of the hind paw of the rabbit was shaved in order to prevent exiting blood from being absorbed to the fur during later bleeding. The apex of the cutis was injured by means of a claw forceps. Immediately thereafter, filters were arranged underneath the wound in such a manner that the blood could directly drop onto the filter without being drawn up from this by capillary effect. Destruction of a forming blood clot was prevented through this precaution. The filters were changed every two minutes and the exiting blood was collected in fractions. Blood collection was continued for 30 minutes. The qualification of bleeding characteristics was conducted by extraction of the blood collected in fractions on the filter with 5 ml each of 0.04% ammonium hydroxide solution over 5 hours. Thereby, the erythrocytes which were collected with the blood in the filter were lysed. During a 10 minute ultrasound treatment, hemoglobin was extracted and quantitatively measured photometrically at 416 nm against a calibration curve, whereby the calibration curve was established by pipetting rabbit blood volumes between 10 $\mu$l and 1 ml onto the filters, extracting as described above, and measuring the hemoglobin photometrically at 416 nm. Accordingly, linear calibration curves could be prepared which made possible a direct conversion of the hemoglobin concentration to the amount of blood per filter. The bleeding characteristics of the nail cut were established as the cumulative loss of blood through additive graphic plotting of the individual blood fractions against time. The increase of cumulative bleeding between 10 and 20 minutes of the experiment was employed as a relevant criterion of bleeding and served as a measurement for the bleeding intensity. The average hemorrhage intensity of animals treated in this method is given in the Figure (FIG. 1).

For testing the active substances, a solution of a pharmaceutical composition containing the respective active ingredients in a volume of 30 ml was continuously infused after inhibitor-induced bleeding in the rabbit with an infusion rate of 1 ml/min and, simultaneously with the beginning of the infusion, the bleeding intensity was re-established as described above. Accordingly, a FEIBA preparation produced according to A 350 726 or A 368 883, was administered in a dose of 75 U/FEIBA/kg to correspondingly pretreated rabbits. This dosage led to a drastic reduction in the bleeding intensity (see FIG. 1).

As a control, a buffer without active ingredient was infused which led to no reduction of bleeding. Equally, the administration of FEIBA in a dose of 5 U/kg led to no significant reduction of bleeding intensity.

In contrast, when a preparation according to the invention corresponding to a dose of 5 U FEIBA/kg and 50 U Factor VIIa/kg was given to the rabbits, a reduction in the bleeding intensity resulted comparable with an effective FEIBA dosage, while 50 U Factor VIIa/kg had no effect on the abnormally increased hemorrhage intensity.

TABLE 1

Purification of FVIIa, Analysis of the intermediate products

| Step | FVII-Coagulation Thromboplastin human | | FVIIa-Coagulation Thromboplastin bovine | | bovine/ human degree of activation |
|---|---|---|---|---|---|
| | spec. activity U/mg | purification factor | spec. activity U/mg | purification factor | |
| FEIBA-supernatant | 0.013 | 1 | 0.018 | 1 | 1.26 |
| Aluminum hydroxide eluate | 14.4 | 1068 | 62.9 | 3559 | 4.17 |
| Q-Sepharose activation | 89.0 | 6591 | 447.8 | 25338 | 4.78 |
| Phenylsepharose Pool | 276.0 | 20448 | 1716.4 | 97128 | 6.59 |
| Q-Sepharose Pool | 820.2 | 60757 | 5408.3 | 306057 | 6.95 |
| Ultraconcentrate (with Alb.) | 4.6 | | 29.5 | | |
| Lyophilisate | 4.0 | | 42.2 | | |
| 10 h/60° C. | 4.1 | | 46.7 | | |
| 10 h/60° C. + 1 h/80° C. | 4.2 | | 36.2 | | |

We claim:

1. A pharmaceutical composition with FEIB-activity for treating a patient with a blood coagulation disorder selected from the group consisting of blood coagulation deficienxcy and blood coagulation inhibition, comprising Factor VII$a$ and at least one additional active ingredient, wherein the composition has an activity of at least 10 Factor VII$a$ units per unit FEIB-activity, and FEIB-activity of more than 5 U/ml.

2. The pharmaceutical composition according to claim 1, wherein the composition has an activity of 10 to 100 Factor VII$a$ units per unit FEIB-activity.

3. The pharmaceutical composition according to claim 2, wherein the composition has an activity of 10 to 20 Factor VII$a$ units per unit FEIB-activity.

4. The pharmaceutical composition according to claim 3, wherein the composition has an activity of 10 to 15 Factor VII$a$ units per unit FEIB-activity.

5. The pharmaceutical composition according to claim 1, wherein the additional active ingredient is selected from the group consisting of Factor II, Factor IX, Factor IX$a$, Factor X and Factor X$a$.

6. The pharmaceutical composition according to claim 5, wherein the additional active ingredient is present in a range of 0.5 to 2 activity units per unit FEIB-activity.

7. The pharmaceutical composition according to claim 6, wherein the additional active ingredient is present in a range of 0.5 to 1.5 activity units per unit FEIB-activity.

8. The pharmaceutical composition according to claim 1, further comprising at least one protein selected from the group consisting of protein C and protein S.

9. A pharmaceutical composition according to claim 1, wherein the composition includes a purified prothrombin complex and the specific activity of Factor VII$a$ greater than 10 U/mg total protein.

10. A pharmaceutical composition according to claims 1, wherein the composition includes a purified partial prothrombin complex and the specific activity of Factor VII$a$ greater than 10 U/mg total protein.

11. A pharmaceutical composition according to claim 9, wherein the prothrombin complex is an activated prothrombin complex or a FEIBA preparation.

12. A pharmaceutical composition according to claim 10, wherein the purified partial prothrombin complex is an activated prothrombin complex or a FEIBA preparation.

13. A pharmaceutical composition according to claims 5, wherein the Factor VII$a$ and additional ingredient are obtained from the same plasma pool.

* * * * *